United States Patent
Teobald

(10) Patent No.: US 6,767,910 B1
(45) Date of Patent: Jul. 27, 2004

(54) TRIAZOLO[4,5-D]PYRIMIDINYL COMPOUNDS

(75) Inventor: Barry Teobald, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 43 days.

(21) Appl. No.: 10/070,211

(22) PCT Filed: Sep. 11, 2000

(86) PCT No.: PCT/GB00/03474

§ 371 (c)(1),
(2), (4) Date: Sep. 3, 2002

(87) PCT Pub. No.: WO01/19826

PCT Pub. Date: Mar. 22, 2001

(30) Foreign Application Priority Data

Sep. 15, 1999 (SE) .............................................. 9903290

(51) Int. Cl.$^7$ ..................... C07D 487/04; A61K 31/519
(52) U.S. Cl. .................................... 514/261.1; 544/254
(58) Field of Search ....................... 544/254; 514/261.1

(56) References Cited

FOREIGN PATENT DOCUMENTS

| EP | 0508687 A | 10/1992 |
|---|---|---|
| WO | WO 9905114 A | 2/1999 |
| WO | WO 9905143 A | 2/1999 |
| WO | WO 0034283 A | 6/2000 |

OTHER PUBLICATIONS

Clemetson, PubMed Abstract (Haemostasis, 29(1):16–26), Sep. 1999.*

Cavallini et al., PubMed Abstract (Ital. Heart J. (3 Suppl): 286–96), Mar. 2002.*

Goldschmidt–Clermont et al., PubMed Abstract (J. Invasive Cardiol. Suppl E: 18E–25E; quiz 26E), Dec. 2002.*

Yen–Shi Lai et al., Synthesis and Protein Kinase C Inhibitory Activities of Balanol Analogs with Replacement of the Perhydroazepine Moiety, Journal of Medicinal Chemistry, vol. 40, No. 2, 1997, pp. 226–235, XP–002162230, American Chemical Society, Washington, US, ISSN: 0022–2623, Compound 18.

S. E. Shaus, et al., Practical Synthesis of Enantiopure Cyclic 1,2–Amino Alcohols via Catalytic Asymmetric Ring Opening of Meso Epoxides, Journal of Organic Chemistry, vol. 62, No. 12, 1997, pp. 4197–4199, XP002162231, American Chemical Society, Easton, US, ISSN 0022–3263, compounds 6 and 7.

Kiguchi et al., Radical cyclization in Heterocycle Synthesis. Part 9: A Novel Synthesis of Aminocyclitols and Related Compounds via Stannyl Radical Cyclization of Oxime Ethers Derived from Sugars, Tetrahedron, vol. 56, 2000, pp. 5819–5833, XP002162232., Elsevier Science Publishers, Amsterdam, NL, ISSN: 0040–4020, compounds 24b and 24d.

* cited by examiner

Primary Examiner—Deepak Rao
(74) Attorney, Agent, or Firm—Ropes & Gray LLP

(57) ABSTRACT

Compounds of the formula (I) and their use as anti-platelet aggregation compounds.

13 Claims, No Drawings

TRIAZOLO[4,5-D]PYRIMIDINYL COMPOUNDS

This application is a National Stage of International Application No. PCT/GB00/03474 filed Sep. 11, 2000.

FIELD OF THE INVENTION

The present invention provides novel hydroxypyrrolidine compounds, their use as medicaments, compositions containing them and processes for their preparation.

BACKGROUND OF THE INVENTION

Platelet adhesion and aggregation are initiating events in arterial thrombosis. Although the process of platelet adhesion to the sub-endothelial surface may have an important role to play in the repair of damaged vessel walls, the platelet aggregation that this initiates can precipitate acute thrombotic occlusion of vital vascular beds, leading to events with high morbidity such as myocardial infarction and unstable angina. The success of interventions used to prevent or alleviate these conditions, such as thrombolysis and platelet-mediated occlusion or re-occlusion also compromises angioplasty.

A number of converging pathways lead to platelet aggregation. Whatever the initial stimulus, the final common event is a cross-linking of platelets by binding of fibrinogen to a membrane-binding site, glycoprotein IIb/IIIa (GPIIb/IIIa). The high anti-platelet efficacy of antibodies or antagonists for GPIIb/IIIa is explained by their interference with this final common event. However, this efficacy may also explain the bleeding problems that have been observed with this class of agent. Thrombin can produce platelet aggregation largely independently of other pathways but substantial quantities of thrombin are unlikely to be present without prior activation of platelets by other mechanisms. Thrombin inhibitors such as hirudin are highly effective anti-thrombotic agents, but again may produce excessive bleeding because they function as both anti-platelet and anti-coagulant agents (The TIMI 9a Investigators (1994), *Circulation* 90, pp. 1624–1630; The Global Use of Strategies to Open Occluded Coronary Arteries (GUSTO) IIa Investigators (1994) *Circulation* 90, pp. 1631–1637; Neuhaus K. L. et. al. (1994) *Circulation* 90, pp. 1638–1642).

It has been found that ADP acts as a key mediator of thrombosis. ADP-induced platelet aggregation is mediated by the $P_{2T}$ receptor subtype located on the platelet membrane. The $P_{2T}$ receptor (also known as $P2Y_{ADP}$ or $P2T_{AC}$) is primarily involved in mediating platelet aggregation/activation and is a G-protein coupled receptor. The pharmacological characteristics of this receptor have been described, for example, in the references by Humphries et al., *Br. J. Pharmacology*, (1994). 113, 1057–1063, and Fagura et al., *Br. J. Pharmacology* (1998) 124, 157–164. Recently it has been shown that antagonists at this receptor offer significant improvements over other anti-thrombotic agents (see *J. Med. Chem.* (1999) 42, 213). There is a need to find $P_{2T}$ ($P2Y_{ADP}$ or $P2T_{AC}$) antagonists as anti-thrombotic agents.

DESCRIPTION OF THE INVENTION

In a first aspect the invention provides a compound of formula (I):

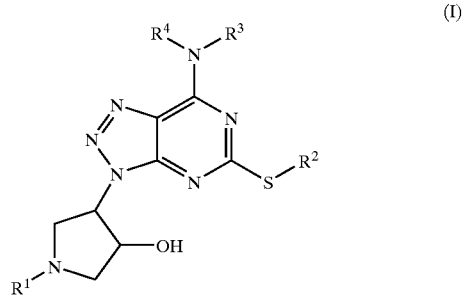

(I)

wherein:
$R^1$ is H, $CH_2R^5$ or $COR^6$;
$R^2$ is alkyl $C_{1-6}$ or alkenyl $C_{1-6}$, optionally substituted by one or more groups selected from alkyl $C_{1-6}$, halogen;
$R^3$ is cycloalkyl $C_{3-8}$, optionally substituted by $R^7$;
$R^4$ is H or alkyl $C_{1-6}$, optionally substituted by one or more halogens;
$R^5$ is H, phenyl or alkyl $C_{1-6}$, optionally substituted by halogen, $OR^8$, phenyl;
$R^6$ is $OR^9$ or alkyl $C_{1-6}$, optionally substituted by one or more groups selected from halogen, $OR^{10}$, phenyl;
$R^7$ is phenyl, optionally substituted by one or more groups selected from alkyl $C_{1-6}$, halogen, $OR^8$;
$R^8$, $R^9$ and $R^{10}$, are independently H or alkyl $C_{1-6}$, optionally substituted by one or more groups selected from halogen or alkyl $C_{1-6}$;
or a pharmaceutically acceptable salt or solvate thereof, or a solvate of such a salt.

Preferably the compound of formula (I) has the following stereochemistry:

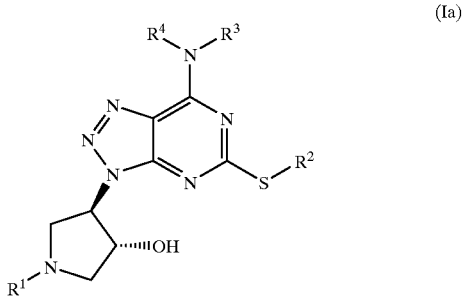

(Ia)

Where $R^3$ is

the stereochemistry is preferably

Preferably $R^1$ is H, $CH_2Ph$, $CH_2CH_2OH$, or $CO_2tBu$.
Preferably $R^2$ is n-Pr.

Preferably R³ is cycloalkyl C₃₋₈ substituted by phenyl.

Preferably R⁴ is H or methyl.

Compounds of the invention include:

[3R-[3α,4β(1R*,2S*)]]-4-[7-[(2-Phenylcyclopropyl)amino]-5-(propylthio)-3H-[1,2,3]triazolo[4,5-d]pyrimidin-3-yl]-3-pyrrolidinol;

[3S-[3α,4β(1S*,2R*)]]-3-Hydroxy-4-[7-[(2-phenylcyclopropyl)amino]-5-(propylthio)-3H-[1,2,3]triazolo[4,5-d]pyrimidin-3-yl]-1-pyrrolidinecarboxylate, 1,1-dimethylethyl ester,

[3S-[3α,4β(1R*,2S*)]]-3-Hydroxy-4-[7-[(2-phenylcyclopropyl)amino]-5-(propylthio)-3H-[1,2,3]triazolo[4,5-d]pyrimidin-3-yl]-1-pyrrolidinecarboxylate, 1,1-dimethylethyl ester,

[3S-[3α,4β(1S*,2R*)]]-4-[7-[(2-Phenylcyclopropyl)amino]-5-(propylthio)-3H-[1,2,3]triazolo[4,5-d]pyrimidin-3-yl]-3-pyrrolidinol;

[3R-[3α,4β(1R*,2S*)]]-4-[7-[N-Methyl-N-(2-phenylcyclopropyl)amino]-5-(propylthio)-3H-[1,2,3]triazolo[4,5-d]pyrimidin-3-yl]-3-pyrrolidinol,

[3R-[3α,4β(1R*,2S*)]]-1-Hydroxyethyl-4-[7-[(2-phenylcyclopropyl)amino]-5-(propylthio)-3H-[1,2,3]triazolo[4,5-d]pyrimidin-3-yl]-3-pyrrolidinol;

[3R-[3α,4β(1R*,2S)]]-4-[7-[(2-Phenylcyclopropyl)amino]-5-(propylthio)-3H-[1,2,3]triazolo[4,5-d]pyrimidin-3-yl]-1-(phenylmethyl)-3-pyrrolidinol;

[3R-[3α,4β(1R*,2S*)]]-1-Acetyl-4-[7-[(2-phenylcyclopropyl)amino]-5-(propylthio)-3H-[1,2,3]triazolo[4,5-d]pyrimidin-3-yl]-3-pyrrolidinol.

or a pharmaceutically acceptable salt or solvate thereof, or a solvate of such a salt.

The invention further provides a process for the preparation of a compound of formula (I) which comprises:

a. For compounds of formula (I) where R¹ is H, reacting a compound of formula (II):

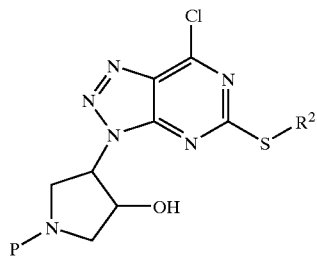

(II)

wherein R² is as defined above and P is a protecting group, preferably t-BuOCO, with R³R⁴NH, wherein R³ and R⁴ are as defined in (I), and a base, preferably triethylamine or N,N-diisopropylethylamine, in the presence of an inert solvent preferably acetonitrile, preferably at a temperature between about 20° C. and about 100° C. and optionally thereafter removing any protecting groups.

Examples of protecting groups include t-BuOCO and CH₂Ph. Protecting groups can be added and removed using known reaction conditions. The use of protecting groups is fully described in 'Protective Groups in Organic Chemistry', edited by J W F McOmie, Plenum Press (1973), and 'Protective Groups in Organic Synthesis', 2nd edition, T W Greene & P G M Wutz, Wiley-Interscience (1991).

A compound of formula (II) can be prepared by diazotizing a compound of formula (III):

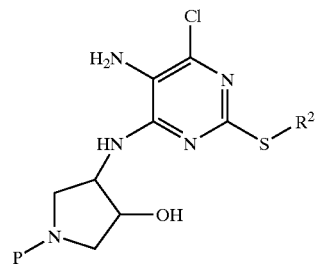

(III)

where R² and P are defined above, and where necessary other reactive groups might also be protected, with a C₁₋₆ alkyl nitrite, preferably iso-amylnitrite in the presence of an inert solvent preferably acetonitrile at a temperature of between about 20 and about 80° C., or with an alkali metal nitrite, preferably sodium nitrite, under aqueous acidic conditions, preferably aqueous hydrochloric or acetic acid and preferably at a temperature between about 0° C. and about 20° C.

A compound of formula (III) can be prepared by reacting a compound of formula (IV):

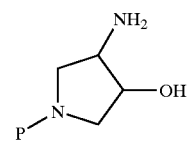

(IV)

wherein P is a protecting group, with a compound of formula (V):

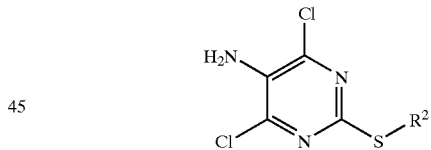

(V)

wherein R² is as defined in formula (I) and is preferably n-propyl. The reaction is carried out in the presence of a base, preferably triethylamine or N,N-diisopropylethylamine, in an inert solvent preferably N,N-dimethylformamide or n-butanol, at a temperature between about 100° C. and about 150° C.

The preparation of the formula (IV) racemate is described in Okada et al., Chem. Pharm. Bull. (1993), 41, 132–8; the preparation of formula (IV) enantiomers is described in Schaus, et al., J. Org. Chem. (1997), 62, 4197–9; the preparation of a compound of formula V (R² is n-propyl) is described in EP 508687.

Compounds of formula (I) where R² is other than n-propyl are prepared by displacement of the sulphone group from a compound of formula (VI):

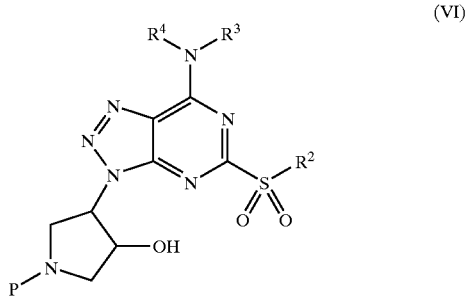

(VI)

where $R^2$ is n-propyl, P, $R^3$ and $R^4$ are defined above, using either a sodium alkylthiolate ($R^2$SNa) in the presence of an inert solvent, preferably N,N-dimethylformamide, preferably at a temperature between about 0° C. and about 50° C. or sodium hydrosulphide (NaSH, in the presence of an inert solvent preferably N,N-dimethylformamide. The latter reaction is followed by alkylation with an alkyl halide ($R^2$X, where X is a leaving group preferably bromide or iodide), preferably at a temperature between about 0° C. and about 50° C. and optionally thereafter removing any protecting groups.

The preparation of the compound of formula (VI), where $R^2$ is n-propyl, is preferably carried out by reacting a compound of formula (I), where $R^1$ has been protected as described above, with a peracid, preferably m-chloroperbenzoic acid, in the presence of an inert chlorocarbon solvent such as dichloromethane or a mixture of dichloromethane and methanol, at a temperature between about 0° C. and about 50° C.

b. For compounds of formula (I) where $R^1$ is $CH_2R^5$, where $R^5$ is defined in formula (I), the reaction scheme outlined in a above is followed by reductive amination using an aldehyde ($R^5$CHO) and a reducing agent, preferably sodium triacetoxyborohydride, and optionally thereafter removing any protecting groups. The reductive amination reaction is preferably carried out in the presence of an inert solvent preferably N,N-dimethylformamide, tetrahydrofuran or a mixture of acetonitrile and N-methylpyrrolidone and preferably at a temperature between about 0° C. and about 50° C.

c. For compounds of formula (I) where $R^1$ is $COR^6$, where $R^6$ is defined in formula (I), the reaction scheme outlined in a above is followed by acylation using an acid halide ($R^6$COX) or anhydride (($R^6$CO)$_2$O) or an acid ($R^6CO_2H$) in the presence of a suitable activating agent preferably N,N'-carbonyldiimidazole or N,N'-dicyclohexylcarbodiimide, and a base preferably triethylamine or N,N-diisopropylethylamine, and optionally thereafter removing any protecting groups. The acylation is preferably carried out in the presence of an inert solvent preferably dichloromethane, chloroform or tetrahydrofuran and preferably at a temperature between about 0° C. and about 50° C.

Compounds of formula (II), (III), (IV) and (V) form a further aspect of the invention.

Salts of the compounds of formula (I) may be formed by reacting the free base, or a salt or a derivative thereof, with one or more equivalents of the appropriate acid (for example a hydrohalic (especially HCl), sulphuric, oxalic or phosphoric acid). The reaction may be carried out in a solvent or medium in which the salt is insoluble or in a solvent in which the salt is soluble, e.g. water, ethanol, tetrahydrofuran, or diethyl ether, which may be removed in vacuo or by freeze drying. The reaction may also be a metathetical process or it may be carried out on an ion exchange resin. The non-toxic physiologically acceptable salts are preferred, although other salts may be useful, e.g. in isolating or purifying the product.

The compounds of the invention act as $P_{2T}$ ($P2Y_{ADP}$ or $P2T_{AC}$) receptor antagonists. Accordingly, the compounds are useful in therapy, including combination therapy, particularly they are indicated for use as: inhibitors of platelet activation, aggregation and degranulation, promoters of platelet disaggregation, anti-thrombotic agents or in the treatment or prophylaxis of unstable angina, coronary revascularisation procedures including angioplasty (PTCA), myocardial infarction, perithrombolysis, primary arterial thrombotic complications of atherosclerosis such as thrombotic or embolic stroke, transient ischaemic attacks, peripheral vascular disease, myocardial infarction with or without thrombolysis, arterial complications due to interventions in atherosclerotic disease such as angioplasty, endarterectomy, stent placement, coronary and other vascular graft surgery, thrombotic complications of surgical or mechanical damage such as tissue salvage following accidental or surgical trauma, reconstructive surgery including skin and muscle flaps, conditions with a diffuse thrombotic/platelet consumption component such as disseminated intravascular coagulation, thrombotic thrombocytopaenic purpura, haemolytic uraemic syndrome, thrombotic complications of septicaemia, adult respiratory distress syndrome, anti-phospholipid syndrome, heparin-induced thrombocytopaenia and pre-eclampsia/eclampsia, or venous thrombosis such as deep vein thrombosis, venoocclusive disease, haematological conditions such as myeloproliferative disease, including thrombocythaemia, sickle cell disease; or in the prevention of mechanically-induced platelet activation in vivo, such as cardio-pulmonary bypass and extracorporeal membrane oxygenation (prevention of microthromboembolism), mechanically-induced platelet activation in vitro, such as use in the preservation of blood products, e.g. platelet concentrates, or shunt occlusion such as in renal dialysis and plasmapheresis, thrombosis secondary to vascular damage/inflammation such as vasculitis, arteritis, glomerulonephritis, inflammatory bowel disease and organ graft rejection, conditions such as migraine, Raynaud's phenomenon, conditions in which platelets can contribute to the underlying inflammatory disease process in the vascular wall such as atheromatous plaque formation/progression, stenosis/restenosis and in other inflammatory conditions such as asthma, in which platelets and platelet-derived factors are implicated in the immunological disease process. Further indications include treatment of CNS disorders and prevention of the growth and spread of tumours.

In particular, the compounds of the invention are useful in the treatment or prevention of myocardial infarction, thrombotic stroke, transient ischaemic attacks, peripheral vascular disease and stable and unstable angina, especially unstable angina.

The invention also provides a method of treatment or prevention of the above disorders which comprises administering to a patient suffering from or susceptible to such a disorder a therapeutically effective amount of a compound according to the invention.

According to the invention there is further provided the use of a compound according to the invention as an active ingredient in the manufacture of a medicament for use in the treatment or prevention of the above disorders.

The compounds may be administered topically, e.g. to the lung and/or the airways, in the form of solutions, suspensions, HFA aerosols and dry powder formulations; or systemically, e.g. by oral administration in the form of tablets, pills, capsules, syrups, powders or granules, or by parenteral administration in the form of sterile parenteral solutions or suspensions, by subcutaneous administration, or by rectal administration in the form of suppositories or transdermally.

The compounds of the invention may be administered on their own or as a pharmaceutical composition comprising the compound of the invention in combination with a pharmaceutically acceptable diluent, adjuvant or carrier. Particularly preferred are compositions not containing material capable of causing an adverse, e.g. an allergic, reaction.

Dry powder formulations and pressurised HFA aerosols of the compounds of the invention may be administered by oral or nasal inhalation. For inhalation the compound is desirably finely divided. The compounds of the invention may also be administered by means of a dry powder inhaler. The inhaler may be a single or a multi dose inhaler, and may be a breath actuated dry powder inhaler. One possibility is to mix the finely divided compound with a carrier substance, e.g. a mono-, di- or polysaccharide, a sugar alcohol or another polyol. Suitable carriers include sugars and starch. Alternatively the finely divided compound may be coated by another substance. The powder mixture may also be dispensed into hard gelatine capsules, each containing the desired dose of the active compound. Another possibility is to process the finely divided powder into spheres which break up during the inhalation procedure. This spheronized powder may be filled into the drug reservoir of a multidose inhaler, e.g. that known as the Turbuhaler® in which a dosing unit meters the desired dose which is then inhaled by the patient. With this system the active compound with or without a carrier substance is delivered to the patient.

The pharmaceutical composition comprising the compound of the invention may conveniently be tablets, pills, capsules, syrups, powders or granules for oral administration; sterile parenteral or subcutaneous solutions, suspensions for parenteral administration or suppositories for rectal administration.

For oral administration the active compound may be admixed with an adjuvant or a carrier, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution, which may contain e.g. gum arabic, gelatine, talcum, titanium dioxide, and the like. Alternatively, the tablet may be coated with a suitable polymer dissolved either in a readily volatile organic solvent or an aqueous solvent.

For the preparation of soft gelatine capsules, the compound may be admixed with e.g. a vegetable oil or polyethylene glycol. Hard gelatine capsules may contain granules of the compound using either the above mentioned excipients for tablets, e.g. lactose, sacharose, sorbitol, mannitol, starches, cellulose derivatives or gelatine. Also liquid or semisolid formulations of the drug may be filled into hard gelatine capsules.

Liquid preparations for oral application may be in the form of syrups or suspensions, for example solutions containing the compound, the balance being sugar and a mixture of ethanol, water, glycerol and propylene glycol. Optionally such liquid preparations may contain colouring agents, flavouring agents, saccharine and carboxymethylcellulose as a thickening agent or other excipients known to those skilled in art.

EXAMPLES

The invention is illustrated by the following non-limiting examples.

In the examples the NMR spectra wee measured on a Varian Unity Inova 300 or 400 spectrometer and the MS spectra were measured as follows: EI spectra were obtained on a VG 70-250S or Finnigan Mat Incos-XL spectrometer, FAB spectra were obtained on a VG70-250SEQ spectrometer, ESI and APCI spectra were obtained on Finnigan Mat SSQ7000 or a Micromass Platform spectrometer. Preparative HPLC separations were generally performed using a Novapak®, Bondapak® or Hypersil® column packed with BDSC-18 reverse phase silica. Flash chromatography (indicated in the Examples as ($SiO_2$)) was carried out using Fisher Matrix silica, 35–70 μm. For examples which show the presence of rotamers in the proton NMR spectra only the chemical shifts of the major rotamer are quoted.

Example 1

[3R-[3α,4β(1R*,2S*)]]-4-[7-[(2-Phenylcyclopropyl)amino]-5-(propylthio)-3H-[1,2,3]triazolo[4,5-d]pyrimidin-3-yl]-3-pyrrolidinol, trifluoroacetate salt a) (3R,4R)-3-[[5-Amino-6-chloro-2-(propylthio)pyrimidin-4-yl]amino]-4-hydroxy-1-pyrrolidinecarboxylate, 1,1-dimethylethyl ester Triethylamine (18.8 ml) was added to a solution of (3R,4R)-4-amino-3-hydroxy-1-pyrrolidinecarboxylate, 1,1-dimethylethyl ester (prepared as described in J. Org. Chem., 1997, 62, 4197 using the (S,S')(salen)Cr(III)complex) (3.63 g) and 4,6-dichloro-2-propylthiopyrimidine-5-amine (prepared as described in EP508687) (3.56 g) and the resulting mixture was heated at 100° C. for 24 hours. The excess triethylamine was removed in vacuo and the residue was diluted with water and extracted with ethyl acetate. The organic phase was washed with brine, dried and concentrated in vacuo. The residue was purified by chromatography ($SiO_2$, dichloromethane:methanol, 97:3 as eluant) followed by trituration with diethylether/iso-hexane to give the sub-title compound (4.16 g).

MS (APCI) 404 (M+H$^+$, 100%).

b) (3R,4R)-4-[7-Chloro-5-(propylthio)-3H-[1,2,3]triazolo[4,5-d]pyrimidin-3-yl]-3-hydroxy-1-pyrrolidinecarboxylate, 1,1-dimethylethyl ester The product from step a) (4.1 g) and iso-amylnitrite (2.74 ml) were heated under reflux in acetonitrile (20 ml) for 1 hour. The reaction mixture was concentrated in vacuo and the residue purified by chromatography ($SiO_2$, ethyl acetate:iso-hexane, 1:4 as eluant) to afford the sub-title compound (3.32 g).

MS (APCI) 415 (M+H$^+$, 100%).

c) [3R-[3α,4β(1R*,2S*)]]-3-Hydroxy-4-[7-[(2-phenylcyclopropyl)amino]-5-(propylthio)-3H-[1,2,3]triazolo[4,5-d]pyrimidin-3-yl]-1-pyrrolidinecarboxylate, 1,1-dimethylethyl ester N,N-diisopropylethylamine (3 ml) was added to a solution of the product from step b) (1.2 g) and (1R-trans)-2-phenylcyclopropanamine, [R-(R*,R*)]-2,3-dihydroxybutanedioate (1:1) (prepared as described by L. A. Mitscher et al., J. Med. Chem., 1986, 29, 2044) (1.23 g) in dichloromethane (40 ml). The reaction mixture was stirred at room temperature for 16 hours then washed with water. The organic phase was washed with dilute hydrochloric acid and brine, dried and concentrated in vacuo. The residue was purified by chromatography (SiO$_2$, dichloromethane:methanol, 99:1 as eluant) to afford the sub-title compound (1.12 g).

MS (APCI) 512 (M+H$^+$, 100%).

d) [3R-[3α,4β(1R*,2S*)]]-4-[7-[(2-Phenylcyclopropyl) amino]-5-(propylthio)-3H-[1,2,3]triazolo[4,5-d]pyrimidin-3-yl]-3-pyrrolidinol, trifluoroacetate salt The product from step c) (0.54 g) was dissolved in trifluoroacetic acid (22.5 ml) and water (25 ml) and the solution stirred at room temperature for 4 h. The solvents were evaporated and the residue dried by azeotropic distillation with toluene (4×50 ml) followed by methanol (50 ml) to give a yellow foam. The crude product was triturated with diethylether (50 ml) to afford a white powder that was recrystallised (ethyl acetate) to afford the title compound (0.37 g) as a white solid.

MS (APCI) 412 (M+H$^+$, 100%)

NMR δH (d$_6$-DMSO) 9.5 (2H, br s), 9.47 (1H, d), 7.10–7.35 (5H, m), 6.28 (1H, d), 5.26 (1H, br m), 4.65 (1H, br s), 3.90 (2H, m), 3.52 (1H, d,AB), 3.3 (1H, m), 3.24 (1H, m), 2.8–3.0 (2H, t,AB), 2.13 (1H, m), 1.54 (1H, d,t), 1.47 (2H, sext.), 1.34 (1H, br q), 0.79 (3H, t).

Example 2

[3S-[α,4β(1S*,2R*)]]-3-Hydroxy-4-[7-[(2-phenylcyclopropyl)amino]-5-(propylthio)-3H-[1,2,3]triazolo[4,5-d]pyrimidin-3-yl]-1-pyrrolidinecarboxylate, 1,1-dimethylethyl ester a) (3S,4S)-3-[[5-Amino-6-chloro-2-(propylthio)pyrimidin-4-yl]amino]-4-hydroxy-1-pyrrolidinecarboxylate, 1,1-dimethylethyl ester Prepared according to the method of Example 1, step a) using (3S,4S)-4-amino-3-hydroxy-1-pyrrolidinecarboxylate, 1,1-dimethylethyl ester (prepared as described in J. Org. Chem., 1997, 62, 4197 using a(R,R)(salen)Cr(III)complex).

MS (APCI) 404/406 (M+H$^+$), 404 (100%).

b) (3S,4S)-4-[7-Chloro-5-(propylthio)-3H-[1,2,3]triazolo[4,5-d]pyrimidin-3-yl]-3-hydroxy-1-pyrrolidinecarboxylate, 1,1-dimethylethyl ester Prepared according to the method of Example 1, step b).

MS (APCI) 315 (M+H-BOC$^+$, 100%).

c) [3S-[3α,4β(1S*,2R*)]]-3-Hydroxy-4-[7-[(2-phenylcyclopropyl)amino]-5-(propylthio)-3H-[1,2,3]triazolo[4,5-d]pyrimidin-3-yl]-1-pyrrolidinecarboxylate, 1,1-dimethylethyl ester Prepared according to the method of Example 1, step c).

MS (APCI) 512 (M+H$^+$, 100%).

NMR δH (d$_6$-DMSO) 9.40 (1H, d), 7.31–7.27 (2H, m), 7.20–7.15 (3H, m), 5.78–5.76 (1H, m), 5.11–5.06 (1H, m), 4.61–4.56 (1H, m), 3.94–3.81 (2H, m), 3.69–3.62 (1H, m), 3.30–3.18 (2H, m), 3.11–2.80 (2H, m), 2.15–2.10 (1H, m), 1.73–1.23 (13H, m), 0.80 (3H, t).

Example 3

[3S-[3α,4β(1R*,2S*)]]-3-Hydroxy-4-[7-[(2-phenylcyclopropyl)amino]-5-(propylthio)-3H-[1,2,3]triazolo[4,5-d]pyrimidin-3-yl]-1-pyrrolidinecarboxylate, 1,1-dimethylethyl ester a) [3S-[3α,4β(1R*,2S*)]]-3-Hydroxy-4-[7-[(2-phenylcyclopropyl)amino]-5-(propylthio)-3H-[1,2,3]triazolo[4,5-d]pyrimidin-3-yl]-1-pyrrolidinecarboxylate, 1,1-dimethylethyl ester Prepared according to the method of Example 2, step c) using (1S-trans)-2-phenyl-cyclopropanamine, [S-(R*,R*)-2, 3-dihydroxybutanedioate (1:1) (prepared as described by L. A. Mitscher et al., J. Med. Chem., 1986, 29, 2044).

MS (APCI) 512 (M+H$^+$, 100%).

NMR δH (d$_6$-DMSO) 9.40 (1H, d), 7.31–7.27 (2H, m), 7.20–7.15 (3H, m), 5.78–5.76 (1H, m), 5.11–5.06 (1H, m), 4.624.58 (1H, m), 3.94–3.81 (2H, m), 3.69–3.63 (1H, m), 3.30–3.18 (2H, m), 3.11–2.80 (2H, m), 2.15–2.11 (1H, m), 1.72–1.23 (13H, m), 0.80 (3H, t).

Example 4

[3S-[3α,4β(1S*,2R*)]]-4-[7-[(2-Phenylyclopropyl)amino]-5-(propylthio)-3H-[1,2,3]triazolo[4,5-d]pyrimidin-3-yl]-3-pyrrolidinol, trifluoroacetate salt a) [3S-[3α,4β(1S*,2R*)]]-4-[7-[(2-Phenylcyclopropyl)amino]-5-(propylthio)-3H-[1,2,3]triazolo[4,5-d]pyrimidin-3-yl]-3-pyrrolidinol, trifluoroacetate salt Prepared according to the method of Example 1, step d) using the compound of Example 2, step c).

MS (APCI) 412 (M+H$^+$, 100%).

NMR δH (d$_6$-DMSO) 9.5 (2H, br s), 9.48 (1H, d), 7.10–7.35 (5H, m), 6.30 (1H, d), 5.26 (1H, br m), 4.64 (1H, br s), 3.9 (2H, m), 3.5 (1H, d,AB), 3.26 (1H, m), 3.24 (1H, m), 2.7–3.0 (2H, t,AB), 2.11 (1H, m), 1.55 (11H, d,t), 1.46 (2H, sext.), 1.34 (1H, br q), 0.78 (3H, t).

Example 5

[3R-[3α,4β(1R,2S*)]]-4-[7-[N-Methyl-N-(2-phenylcyclopropyl)amino]-5-(propylthio)-3H-[1,2,3]triazolo[4,5-d]pyrimidin-3-yl]-3-pyrrolidinol, trifluoroacetate salt a) [3R-[3α,4β(1R*,2S*)]]-3-Hydroxy-4-[7-[N-methyl-N-(2-phenylcyclopropyl)amino]-5-(propylthio)-3H-[1,2,3]triazolo[4,5-d]pyrimidin-3-yl]-1-pyrrolidinecarboxylate, 1,1-dimethylethyl ester.

N,N-diisopropylethylamine (0.5 ml) was added to a solution of the product from Example 1 step b) (0.3 g) and (1R-trans)-N-methyl-2-phenylcyclopropylamine hydrochloride (prepared as described by C. Kaiser et al, J. Org. Chem., 1962, 27, 768–773, using (1R-trans)-2-phenylcyclopropanamine, [R-(R*,R*)]]-2,3-dihydroxybutanedioate (1:1) (prepared as described by L. A Mitscher et al, J. Med. Chem., 1986, 29, 2044) (0.2 g) in dichloromethane (20 ml). The reaction mixture was stirred at room temperature for 48 hours then washed with water. The organic phase was washed with dilute hydrochloric acid and brine, dried and concentrated in vacuo. The residue was purified by chromatography (SiO$_2$, dichloromethane:methanol, 99:1 as eluant) to afford the sub-title compound (0.36 g).

MS (APCI) 470 (M+H$^+$, 100%).

b) [3R-[3α,4β(1R*,2S*)]]-4-[7-[N-Methyl-N-(2-phenylcyclopropyl)amino]-5-(propylthio)-3H-[1,2,3]triazolo[4,5-d]pyrimidin-3-yl]-3-pyrrolidinol, trifluoroacetate salt A solution of the product from step a) (0.36 g) in 9:1 trifluoroacetic acid:water (10 ml) was stirred at room temperature for 2 hours. The solvent was removed and co-evaporated with toluene (3×). The residue was dissolved in water (20 ml) and ethanol (1 ml) and freeze-dried for 16 hours to give the title compound (0.33 g).

MS (APCI) 426 (M+H$^+$, 100%).

NMR δH (d$_6$-DMSO) 9.33 (2H, br s), 7.29 (2H, m), 7.20 (3H, m), 6.04 (1H, br s), 5.27 (1H, m), 4.72 (1H, d), 3.84–3.97 (2H, m), 3.56 (4H, m), 3.31 (1H, d), 3.06 (3H, under DMSO), 2.43 (1H, under H$_2$O), 1.54–1.66 (3H, m), 1.45 (1H, m), 0.94 (3H, t).

Example 6

[3R-[3α,4β(1R*,2S*)]]-1-Hydroxyethyl-4-[7-[(2-phenylcyclopropyl)amino]-5-(propylthio)-3H-[1,2,3]triazolo[4,5-d]pyrimidin-3-yl]-3-pyrrolidinol, trifluoroacetate salt a) [3R-[3α,4β(1R*,2S*)]]-1-[2-[(1,1-Dimethylethyl)(dimethyl)silyl]oxy]ethyl-4-[7-[(2-phenylcyclopropyl)amino]-5-(propylthio)-3H-[1,2,3]triazolo[4,5-d]pyrimidin-3-yl]-3-pyrrolidinol.

[[(1,1-Dimethylethyl)dimethylsilyl]oxy]acetaldehyde (Tet. Lett., 1995, 36, 6033) (0.27 g) was added to a solution of the product from Example 1 step d) (0.4 g) and sodium triacetoxyborohydride (0.48 g) in dry tetrahydrofuran (10 ml) and the mixture was stirred at room temperature for 16 hours. The reaction mixture was diluted with water and extracted with ethyl acetate (thrice). The combined organic phase was washed with brine, dried and concentrated in vacuo. The residue was purified by chromatography (SiO$_2$, dichloromethane:methanol, 99:1 as eluant) to give the sub-title compound (0.2 g).

MS (APCI) 570 (M+H$^+$, 100%).

b) [3R-[3α,4β(1R*,2S*)]]-1-Hydroxyethyl-4-[7-[(2-phenylcyclopropyl)amino]-5-(propylthio)-3H-[1,2,3]triazolo[4,5-d]pyrimidin-3-yl]-3-pyrrolidinol, trifluoroacetate salt Tetrabutylammonium fluoride hydrate (0.2 g) was added to a solution of the product from step a) (0.2 g) in dry tetrahydrofuran (10 ml) and the mixture was stirred at room temperature for 16 hours. The solvent was removed in vacuo and the residue was purified by chromatography (SiO$_2$, dichloromethane:methanol, 95:5 as eluant). Trifluoroacetic acid (22 μl) was added to a solution of the resulting oil in diethylether (5 ml) and the solid formed was collected by filtration to give the title compound (0.12 g).

MS (APCI) 456 (M+H$^+$, 100%).

NMR δH (d$_6$-DMSO+D$_2$O) 7.31 (2H, m), 7.21 (3H, m), 5.36 (1H, br s), 4.87 (1H, br s), 4.18 (1H, m), 4.04 (1H, m), 3.82 (3H, m), 3.55 (1H, under H$_2$O), 3.45 (2H, m), 3.29 (1H, br s), 3.02 (2H, br s), 2.22 (1H, br s), 1.58 (2H, br s), 1.50 (1H, m), 1.36 (1H, m), 0.88 (3H, br s).

Example 7

[3R-[3α,4β(1R*,2S*)]]-4-[7-[(2-Phenylcyclopropyl)amino]-5-(propylthio)-3H-[1,2,3]triazolo[4,5-d]pyrimidin-3-yl]-1-(phenylmethyl)-3-pyrrolidinol, trifluoroacetate salt Benzaldehyde (0.1 ml) was added to a solution of the product from Example 1 step d) (0.26 g) and sodium triacetoxyborohydride (0.32 g) in dry tetrahydrofuran (10 ml) and the mixture was stirred at room temperature for 3 hours. The reaction mixture was diluted with water and extracted with ethyl acetate (thrice). The combined organic phase was washed with brine, dried and concentrated. Trifluoroacetic acid (20 μl) was added to a solution of the resulting oil in diethylether (5 ml) and the solvent was removed in vacuo. The residue was dissolved in water (20 ml) and ethanol (5 ml) and freeze-dried for 16 hours. Purification by chromatography (HPLC, Novapak® C18 column, 0.1% aqueous trifluoroacetic acid:acetonitrile, gradient elution 75:25 to 0:100 over 15 minutes), followed by freeze drying gave the title compound (0.094 g).

MS (APCI) 502 (M+H$^+$, 100%).

NMR δH (d$_6$-DMSO+D$_2$O) 7.53 (2H, d), 7.48 (3H, m), 7.31 (2H, m), 7.20 (3H, m), 5.34 (1H, m), 4.88 (1H, m), 4.48 (2H, q), 4.05 (1H, m), 3.90 (1H, m), 3.72 (1H, m), 3.41 (1H, m), 3.30 (1H, br m), 3.01 (2H, br m), 2.21 (1H, br s), 1.50–1.56 (3H, m), 1.36 (1H, m), 0.87 (3H, br s).

Example 8

[3R-[3α,4β(1R*,2S*)]]-1-Acetyl-4-[7-[(2-phenylcyclopropyl)amino]-5-(propylthio)-3H-[1,2,3]triazolo[4,5-d]pyrimidin-3-yl]-3-pyrrolidinol A mixture of the product from Example 1 step d) (0.17 g), acetic anhydride (0.046 ml) and pyridine (0.078 ml) in dichloromethane (3 ml) was stirred at room temperature under a nitrogen atmosphere for 16 hours. The reaction mixture was diluted with water and extracted with dichloromethane (twice). The combined organic phase was washed with dilute hydrochloric acid and brine, dried and concentrated in vacuo. The residue was purified by chromatography (SiO$_2$, dichloromethane:methanol, 98:2 as eluant) followed by trituration with acetonitrile to give the title compound (0.06 g).

MS (APCI) 454 (M+H$^+$, 100%).

NMR δH (d$_6$-DMSO) 9.39 (1H, m), 7.30 (2H, m), 7.19 (3H, m), 5.77–5.86 (1H, m), 5.09–5.16 (1H, m), 4.60–4.69 (1H, m), 4.00–4.13 (1H, m), 3.91 (2H, m), 3.46, 3.68 (1H, m), 3.21 (1H, br m), 2.82–2.91 (2H, m), 2.13 (1H, m), 1.98 (3H, d), 1.34–1.54 (4H, m), 0.79 (3H, t).

Pharmacological Data

The preparation for the assay of the P$_{2T}$ (P2Y$_{ADP}$ or P2T$_{AC}$)-receptor agonist/antagonist activity in washed human platelets for the compounds of the invention was carried out as follows.

Human venous blood (100 ml) was divided equally between 3 tubes, each containing 3.2% trisodium citrate (4 ml) as anti-coagulant. The tubes were centrifuged for 15 minutes at 240G to obtain a platelet-rich plasma (PRP) to which 300 ng/ml prostacyclin was added to stabilize the platelets during the washing procedure. Red cell free PRP was obtained by centrifugation for 10 minutes at 125G followed by further centrifugation for 15 minutes at 640G. The supernatant was discarded and the platelet pellet resuspended in modified. Calcium Free Tyrode solution (10 ml) (CFT), composition: NaCl 137 mM, NaHCO$_3$ 11.9 mM, NaH$_2$PO$_4$ 0.4 mM, KCl 2.7 mM, MgCl$_2$ 1.1 mM, dextrose 5.6 mM, gassed with 95% O$_2$/5% CO$_2$ and maintained at 37° C. Following addition of a further 300 ng/ml PGI$_2$, the pooled suspension was centrifuged once more for 15 minutes at 640G. The supernatant was discarded and the platelets resuspended initially in 10 ml CFT with further CFT added to adjust the final platelet count to 2×10$^5$/ml. This final suspension was stored in a 60 ml syringe at 3° C. with air excluded. To allow recovery from PGI$_2$-inhibition of normal function, platelets were used in aggregation studies no sooner than 2 hours after final resuspension.

In all studies, 3 ml aliquots of platelet suspension were added to tubes containing CaCl$_2$ solution (60 μl of 50 mM solution with a final concentrations of 1 mM). Human fibrinogen (Sigma, F 4883) and 8-sulphophenyltheophylline (8-SPT which was used to block any P$_1$-agonist activity of compounds) were added to give final concentrations of 0.2 mg/ml (60 μl of 10 mg/ml solution of clottable protein in saline) and 300 nM (10 μl of 15 nM solution in 6% glucose), respectively. Platelets or buffer as appropriate were added in a volume of 150 μl to the individual wells of a 96 well plate. All measurements were made in triplicate in platelets from each donor.

The agonist/antagonist potency was assessed as follows.

Aggregation responses in 96 well plates were measured using the change in absorbance given by the plate reader at 660 nm. Either a Bio-Tec Ceres 900C or a Dynatech MRX were used as the plate reader.

The absorbance of each well in the plate was read at 660 nm to establish a baseline figure. Saline or the appropriate solution of test compound was added to each well in a volume of 10 μl to give a final concentration of 0, 0.01, 0.1, 1, 10 or 100 mM. The plate was then shaken for 5 min on an orbital shaker on setting 10 and the absorbance read at 660 nm. Aggregation at this point was indicative of agonist activity of the test compound. Saline or ADP (30 mM; 10 μl of 450 mM) was then added to each well and the plate shaken for a further 5 min before reading the absorbance again at 660 nm.

Antagonist potency was estimated as a % inhibition of the control ADP response to obtain an $IC_{50}$. Compounds exemplified have $pIC_{50}$ values of more than 5.0.

What is claimed is:

1. A compound of formula (I):

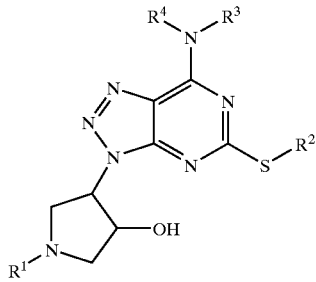

(I)

wherein:

$R^1$ is H, $CH_2R^5$ or $COR^6$;

$R^2$ is alkyl $C_{1-6}$ or alkenyl $C_{1-6}$, optionally substituted by one or more groups selected from alkyl $C_{1-6}$ and halogen;

$R^3$ is cycloalkyl $C_{3-8}$, optionally substituted by $R^7$;

$R^4$ is H or alkyl $C_{1-6}$, optionally substituted by one or more halogens;

$R^5$ is H, phenyl or alkyl $C_{1-6}$, optionally substituted by halogen, $OR^8$, and phenyl;

$R^6$ is $OR^9$ or alkyl $C_{1-6}$, optionally substituted by one or more groups selected from halogen, $OR^{10}$, and phenyl;

$R^7$ is phenyl, optionally substituted by one or more groups selected from alkyl $C_{1-6}$, halogen, and $OR^8$;

$R^8$, $R^9$ and $R^{10}$, are independently H or alkyl $C_{1-6}$, optionally substituted by one or more groups selected from halogen or alkyl $C_{1-6}$;

or a pharmaceutically acceptable salt or solvate thereof, or a solvate of such a salt.

2. A compound of according to claim 1 which is:

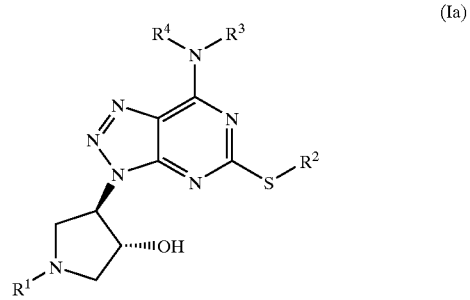

(Ia)

where $R^1$, $R^2$, $R^3$ and $R^4$ are as defined in claim 1.

3. A compound according to claim 1 or 2 in which $R^3$ is

wherein:

$R^7$ is phenyl, optionally substituted by one or more groups selected from alkyl $C_{1-6}$, halogen, and $OR^8$;

$R^8$ is independently H or alkyl $C_{1-6}$, optionally substituted by one or more groups selected from halogen or alkyl $C_{1-6}$.

4. A compound according to claims 1 or 2 in which $R^1$ is H, $CH_2Ph$, $CH_2CH_2OH$, or $CO_2tBu$.

5. A compound according to claims 1 or 2 in which $R^2$ is n-Pr.

6. A compound according to claims 1 or 2 in which $R^3$ is cycloalkyl $C_{3-8}$ substituted by phenyl.

7. A compound according to claims 1 or 2 in which $R^4$ is H or methyl.

8. A compound according to claim 1 which is:

[3R-[3α,4β(1R*,2S*)]]-4-[7-[(2-Phenylcyclopropyl) amino]-5-(propylthio)-3H-[1,2,3]triazolo[4,5-d] pyrimidin-3-yl]-3-pyrrolidinol;

[3S-[3α,4β(1S*,2R*)]]-3-Hydroxy-4-[7-[(2-phenylcyclopropyl)amino]-5-(propylthio)-3H-[1,2,3] triazolo[4,5-d]pyrimidin-3-yl]-1-pyrrolidinecarboxylate, 1,1-dimethylethyl ester;

[3S-[3α,4β(1R*,2S*)]]-3-Hydroxy-4-[7-[(2-phenylcyclopropyl)amino]-5-(propylthio)-3H-[1,2,3] triazolo[4,5-d]pyrimidin-3-yl]-1-pyrrolidinecarboxylate, 1,1-dimethylethyl ester;

[3S-[3α,4β(1S*,2R*)]]-4-[7-[(2-Phenylcyclopropyl) amino]-5-(propylthio)-3H-[1,2,3]triazolo[4,5-d] pyrimidin-3-yl]-3-pyrrolidinol;

[3R-[3α,4β(1R*,2S*)]]-4-[7-[N-Methyl-N-(2-phenylcyclopropyl)amino]-5-(propylthio)-3H-[1,2,3] triazolo[4,5-d]pyrimidin-3-yl]-3-pyrrolidinol;

[3R-[3α,4β(1R*,2S*)]]-1-Hydroxyethyl-4-[7-[(2-phenylcyclopropyl)amino]-5-(propylthio)-3H-[1,2,3] triazolo[4,5-d]pyrimidin-3-yl]-3-pyrrolidinol;

[3R-[3α,4β(1R*,2S*)]]-4-[7-[(2-Phenylcyclopropyl) amino]-5-(propylthio)-3H-[1,2,3]triazolo[4,5-d] pyrimidin-3-yl]-1-(phenylmethyl)-3-pyrrolidinol;

[3R-[3α,4β(1R*,2S*)]]-1-Acetyl-4-[7-[(2-phenylcyclopropyl)amino]-5-(propylthio)-3H-[1,2,3] triazolo[4,5-d]pyrimidin-3-yl]-3-pyrrolidinol;

or a pharmaceutically acceptable salt or solvate thereof, or a solvate of such a salt.

9. A pharmaceutical composition comprising a compound according to claim 1 or 2 in combination with a pharmaceutically acceptable diluent, adjuvant or carrier.

10. A process for the preparation of a compound of formula (I), where $R^1$ is H, which comprises reacting a compound of formula (II)

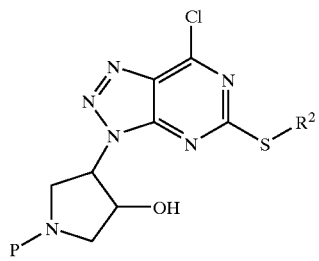

(II)

wherein $R^2$ is as defined in claim 1 and P is a protecting group, with $R^3R^4NH$, wherein $R^3$ and $R^4$ are as defined in claim 1, and a base and optionally thereafter removing any protecting groups.

11. A method of treatment of a platelet aggregation disorder which comprises administering to a person suffering from or susceptible to such a disorder a therapeutically effective amount of compound according to of claim 1 or 2.

12. A method of treatment of myocardial infarction, thrombotic stroke, transient ischaemic attacks, and/or peripheral vascular disease, which comprises administering to a person suffering from or susceptible to such a disorder a therapeutically effective amount of a compound according to claim 1 or 2.

13. A method of treatment of unstable or stable angina, which comprises administering to a person suffering from or susceptible to such a disorder a therapeutically effective amount of a compound according to claim 1 or 2.

* * * * *